United States Patent [19]

Bucalo

BEST AVAILABLE COPY

[11] E Re. 29,061

[45] Reissued Dec. 7, 1976

[54] INTERNAL BLOOD COLLECTION

[75] Inventor: Louis Bucalo, Holbrook, N.Y.

[73] Assignee: Microbyx Corporation, New York, N.Y.

[22] Filed: Sept. 3, 1975

[21] Appl. No.: 609,917

Related U.S. Patent Documents

Reissue of:

[64] Patent No.: 3,867,924
Issued: Feb. 25, 1975
Appl. No.: 329,671
Filed: Feb. 5, 1973

[52] U.S. Cl. ..... 128/2 F; 128/285; 128/DIG. 5

[51] Int. Cl.[2] ..... A61B 5/14; A61F 13/20

[58] Field of Search ..... 128/2 F, 127, 270, 285, 128/275, 272, 290, 296, DIG. 5

[56] References Cited

UNITED STATES PATENTS

| | | | |
|---|---|---|---|
| 2,089,113 | 8/1937 | Chalmers | 128/285 |
| 2,110,962 | 3/1938 | Munro | 128/285 |
| 2,844,150 | 7/1958 | Draghi | 128/285 X |
| 2,905,169 | 9/1959 | Nieburgs | 128/285 |
| 3,371,667 | 3/1968 | Morse | 128/290 R |
| 3,520,300 | 7/1970 | Flower, Jr. | 128/276 |

OTHER PUBLICATIONS

Approved Laboratory Technique, Kolmer et al., 5th Edit., Appleton–Century, Crofts, N.Y. (1959).

*Primary Examiner*—Dalton L. Truluck
*Attorney, Agent, or Firm*—Steinberg & Blake

[57] ABSTRACT

Methods and devices to be used in connection with collection and analyzing of blood. A device which is capable of receiving and holding blood is introduced into the interior of a body cavity where blood is present, and after the device remains in the body cavity for a time sufficient to receive and hold blood, the device is removed and at least part of the blood removed therewith is tested. The device includes an outer holder formed with an entrance through which blood may flow freely into the interior of the holder, and within the holder is a structure such as a body of filamentary material capable of retaining blood in the interior of the holder. This device may be incorporated into a tampon introduced into the vagina for collecting blood during the menstrual cycle.

14 Claims, 5 Drawing Figures.

INTERNAL BLOOD COLLECTION

Matter enclosed in heavy brackets [ ] appears in the original patent but forms no part of this reissue specification; matter printed in italics indicates the additions made by reissue.

BACKGROUND OF THE INVENTION

The present invention relates to the collection of blood.

Thus, it is well known that in order to test the condition of a living being such as a human being or other animal, some of the blood is removed from the living being and is analyzed in a number of different ways. At the present time this blood is derived from the living being by undesirable methods. For example, it is known to prick the tip of a finger, an earlobe, or the like, and in addition it is known to extract blood from an artery with a suitable syringe. These known procedures are highly disadvantageous since an essential part thereof involves wounding the body, creating pain and a certain amount of trauma and requiring not only operations under conditions of high standards of hygiene and sterility to avoid infection but also unavoidable discomfort which follows during healing of the wound required for extraction of blood.

SUMMARY OF THE INVENTION

It is accordingly a primary object of the present invention to provide a method and device which will avoid these drawbacks.

In particular, it is an object of the invention to provide a method and device according to which it is possible to extract and analyze blood without wounding the living being in any way for the purpose of obtaining the blood.

Thus, it is an object of the present invention to take advantage of the presence of blood for any one of a number of different reasons in a cavity of a living being in order to extract some of the latter blood and utilize it for analysis.

It is in particular an object of the present invention to provide a device which can be used at any part of the body of a living creature where blood is present for the purpose of extracting some of this blood so that it can then be analyzed.

Thus, it is an object of the present invention to provide a method and device of the above type which creates no discomfort whatsoever, thus rendering it possible to achieve painless blood extraction without any possibility of infection in connection with the extraction of the blood and without requiring any healing procedures in connection with the extraction of the blood.

According to the invention a device which is capable of receiving and holding blood is introduced into the interior of a cavity of a body of a living creature, this cavity being one in which blood is in any event present. The device is removed from the cavity after the device has remained therein for a period of time sufficient to receive and hold blood, which is thus removed with the device, and then at least part of the latter blood which is removed with the device from the body cavity is tested.

The above device of the invention includes an outer holder which is formed with an entrance means through which blood can flow into the interior of the holder, and within the interior of the holder is a retaining means which is capable of retaining and holding the blood. According to a particular feature of the invention this device may be incorporated into a tampon inserted into the vagina during the menstrual cycle.

BRIEF DESCRIPTION OF DRAWINGS

The invention is illustrated by way of example in the accompanying drawings which form part of this application and in which.

DESCRIPTION OF PREFERRED EMBODIMENTS

According to the present invention advantage is taken of the fact that it is possible to carry out blood tests, in order to check on the condition of a living being such as a human being, for example, with blood which need not be derived from the body by procedures which necessitate piercing through the skin of the body. Thus, up to the present time blood tests have been carried out by extracting blood from an artery or the like with a hyperdermic syringe or by pricking the tip of the finger or the earlobe with a sharp instrument and extracting the blood which flows from the wound. It has been found that it is possible to derive all of the information desired in connection with the condition of the body of a human being or other living creature by checking blood such as blood which flows during the normal menstrual cycle or checking blood which is present in any body cavity such as blood which flows as the result of an operation, blood which is present in any cavity as a result of an injury, or any blood which is encountered in the interior of the body as a result of any illness. Blood of this latter type, which is not extracted from the body especially for the purpose of analysis, also is capable of being analyzed with equal effect.

Figure 1:
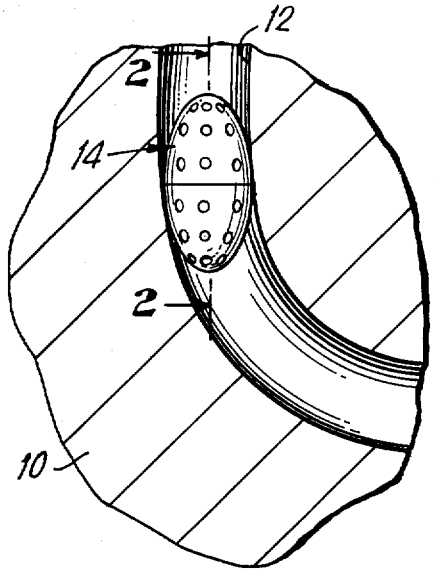
FIG. 1 is a schematic illustration of a device according to the invention situated within a body cavity.

Referring to FIG. 1 there is shown schematically therein a part 10 of a body such as the body of a human being, this part having an internal cavity 12. This cavity may be the vagina or any other cavity such as a sinus passage, the interior of the mouth, the passage leading from the ear, the anal canal, or the like, so that in accordance with the invention any internal body cavity where blood is encountered may be used for the purposes of the present invention. Within this cavity there is inserted in accordance with the invention a device 14 which is small enough to be comfortably received in the body cavity and retained therein while at the same time being large enough to receive and hold an amount of blood sufficient for subsequent analysis. Thus, the device 14 includes an outer holder 16 in the form of a wall which is formed with an entrance means in the form of a plurality of apertures or openings 18 in the illustrated example. In the illustrated example of FIGS. 1 and 2 the holder 16 is made up of a pair of complementary parts 16a and 16b which are provided with mating flanges 17 where they are joined together and where they are releasably retained in connection with each other by friction or by the use of a suitable adhesive if desired. The wall 16 can be made of any material which is compatible with the human body such as any one of a number of different metals and any one of a number of different plastics which will not soften or melt at body temperature. Thus, it is possible to use for this purpose polyethylene, polypropylene, polyvinylchloride, polystyrene, etc. The number of openings 18 is sufficiently great to provide for free entry of blood into the interior of the holder 16.

Within the holder 16 is situated a retaining means 20 which is capable of retaining the blood which flows into the interior of the holder 16 through the entrance means 18. This retaining means 20 preferably takes the form of a body of filamentary material such as cotton wadding, or the like, which is also compatible with the interior of a human being. Instead of cotton wadding it is possible to use a filamentary material such as a compressed body of fine gold wire, since gold is known to be compatible with human beings. Even though a metallic wire filament which does not have absorbent properties is utilized, the surface tension in the blood will cause the blood to be retained at the interstices formed in the interior of the body of compressed wire, and in addition it is to be noted that it is possible to use combinations of filamentary material such as gold wire and cotton, for example. Other filamentary materials may be used to form the retaining means 20 such as, for example, fine monofilaments of plastic. Thus, any plastic compatible with the human body such as nylon, polyesters, and the like, is readily available in fine filamentary form in which it can be compressed into a body held in the holder 16 and forming the retaining means 20.

Figure 2:
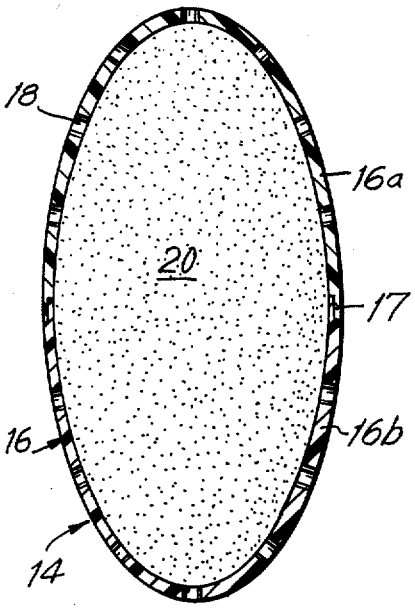
FIG. 2 is a transverse sectional elevation of the device of FIG. 1 taken along line 2—2 of FIG. 1 in the direction of the arrows and showing the device at an enlarged scale.
Figure 3:
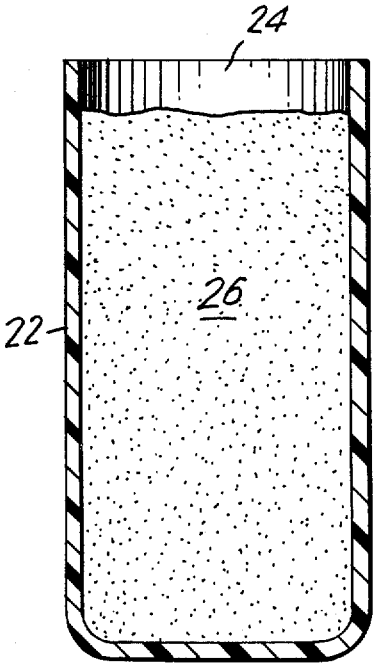
FIG. 3 is a sectional elevation of another embodiment of a device according to the invention.

However, the device of the invention need not take the specific form shown in FIGS. 1 and 2. For example FIG. 3 shows a simple receptacle 22 which may be made of any of the materials used for the wall 16 and which has the form of a simple elongated tube which is open at one end so as to be provided with an entrance means 24 through which the blood may flow freely into the interior of the receptacle 22. This holder or receptacle 22 also has in its interior a retaining means 26 in the form of a compressed body of filamentary material which in the example of FIG. 3 may be cotton wadding.

Figure 4:
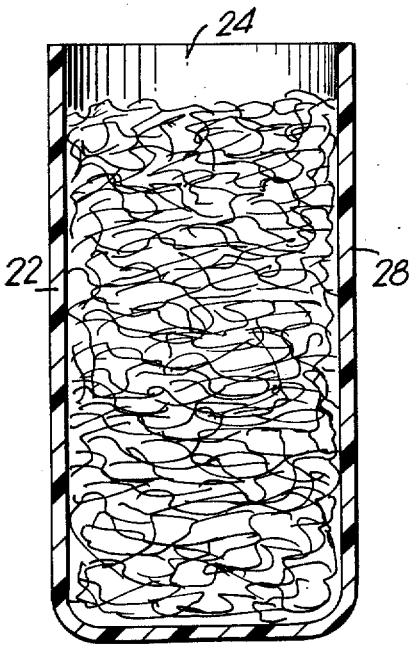
FIG. 4 is a sectional elevation of a further embodiment of a device according to the invention.

In the example of FIG. 4 the receptacle 22 provided with the entrance means 24 is also illustrated, but in this case there is situated within the interior of the holder 22 a retaining means 28 in the form of fine gold wire compressed as illustrated so that blood will be retained along the surface of the wire and at the interstices formed in the body of compressed filamentary material. These bodies 26 and 28 will be retained in the holders 22 simply by frictional pressure against the inner surface of the holder 22.

Figure 5:
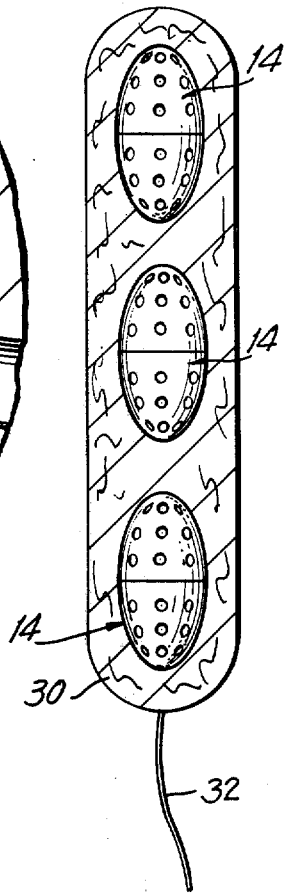
FIG. 5 is a schematic sectional elevation showing how a plurality of the devices of the invention may be incorporated into a tampon.

According to a particular feature of the invention, a tampon 30 may be used as shown in FIG. 5. This is a tampon as is conventionally used by female human beings during the menstrual cycle. Thus, the tampon 30 is introduced into the vagina during the menstrual cycle and has a string 32 extending from the tampon so that it can be removed.

This tampon 30 differs from a conventional tampon in that it has incorporated into the body of the tampon a plurality of the devices of the invention such as the devices 14 described above and shown in FIGS. 1 and 2.

Moreover, with any of the above devices of the invention it is possible to incorporate into the retaining means a suitable blood preservative such as citric acid, for example.

In practicing the method of the invention, the device of the invention is inserted into a body cavity where blood will be encountered. Thus, as pointed out above, the tampon 30 is introduced into the vagina during the menstrual cycle. However, it is possible to introduce any of the devices of FIGS. 1–4 into a cavity such as the anal canal in an individual who is suffering from hemorrhoids, for example. Also, where there is bleeding of the gums in the mouth of a human being or bleeding in the mouth from any source, it is possible to situate a device such as the device 14 or the devices of FIGS. 3 and 4 in the interior of the mouth, wedged between the gums and lips, for example. It is possible to introduce the device of the invention into the ear where bleeding is encountered in the ear. It is also possible to introduce the device into a nostril where bleeding is encountered or into a sinus cavity where bleeding is encountered. Thus, wherever blood is encountered in a body cavity, either as the result of natural functioning of a healthy human being, as would be the case with the tampon 30 of FIG. 5, or as the result of an illness, an operation, or the like at any body cavity, it is possible to use the device of the invention. Thus, in accordance with the method of the invention the device of the invention is inserted into the body cavity and is permitted to remain at the body cavity for a period of time which is sufficient to enable blood to flow freely into the interior of the holder of the device and to be retained by the retaining means therein. Thereafter the device is removed from the interior of the body cavity and the blood in the device can be tested in any conventional manner. For example the two sections 16a and 16b of the device 14 are removed from each other and the means 20 may be used to smear slides which can be examined under the microscope and it can be compressed in any suitable way so as to cause the liquid blood to be compressed out of the body 20 and received in any suitable container to which additional materials are added for testing purposes, as is well known. For example, the blood which is squeezed from the retaining means may be received in a test tube which has in it a known reagent, and such test tubes are then capable of being placed in blood analyzing machines such as well known machines which optically analyze the blood.

It is apparent, therefore, that with the present invention in order to test the blood of an individual it is not necessary to wound the individual and instead it becomes possible to utilize blood which is in any event present at a body cavity for the purpose blood testing.

In the claims which follow, the term "accessible" as used with reference to a cavity of the body is intended to mean a body cavity to which access may be had without requiring any procedures such as piercing a part of the body with a needle, for example. Thus, an "accessible cavity" is intended to mean a body cavity the interior of which is accessible because of the nature of the cavity, such cavities being, for example, the vagina, the mouth, the ear, the nose, the rectum, and the like, all of which are accessible without puncturing or otherwise wounding the body and all of which may at times have internal bleeding which provides a source of blood which may be used with the present invention. In addition, however, the term "accessible" is intended to cover body cavities which become accessible for reasons other than collection of blood. For example any interior part of the body which becomes accessible due to wounding of the body by accident or due to surgical procedures are also considered to be "accessible" in the sense called for by the claims inasmuch as such cavities also are sources of blood which can be collected and tested although these cavities do not become accessible for the purpose of obtaining samples of blood for testing purposes.

What is claimed is:

1. In a method for collecting and analyzing the blood of a living being, the steps of introducing into a body of a living being whose blood is to be analyzed, at a preexisting, accessible cavity of the body which at least temporarily contains blood of the living being, a device having an interior capable of receiving and holding blood which is present in the cavity when the entire device is introduced into and remains wholly within the cavity, [ said device having a blood preservative preliminarily situated in its interior prior to introduction of the device into the body cavity for preserving blood which is received and held in the interior of the device, ] said device being introduced into said cavity at a time which will assure presence of the device in the cavity when blood is present therein, removing the latter device from the body cavity after the device has remained therein for a period of time sufficient to receive and hold blood of the living being, so that blood is removed with the device, *said blood being contacted with a blood preservative for preserving the blood until the same can be tested*, and testing at least part of the blood thus removed from the body cavity with the device.

2. In a method as recited in claim 1 and wherein the living being is a human being.

3. In a method as recited in claim 2 and wherein the human being is a female human being and the cavity is an internal cavity such as the vagina in which blood is present at least periodically as a result of natural functioning of a healthy being.

4. In a method as recited in claim 1 and wherein the cavity into which the device is inserted is a cavity in which blood is present as the result of a normally nonrecurring event such as an illness, an operation, or the like.

5. For use in the collection of blood in a body cavity, a tampon means and at least one device carried by said tampon means for receiving and holding blood which is accessible in the device upon removal of the tampon means from the body cavity, said device including an outer holder formed with an entrance means through which blood can flow freely into the interior of the holder and retaining means situated within and held by the holder for retaining blood in the latter.

6. The combination of claim 5 and wherein said retaining means is in the form of a body of filamentary material.

7. The combination of claim 6 and wherein the filamentary material is cotton.

8. The combination of claim 6 and wherein the filamentary material includes fine gold wire.

9. The combination of claim 5 and wherein said holder is in the form of a wall formed with a plurality of openings which constitute said entrance means and through which blood can enter into the interior of the holder.

10. The combination of claim 5 and wherein said device is at least partially embedded in said tampon means.

11. The combination of claim 10 and wherein said device is entirely embedded within the tampon means for receiving only blood which has first travelled through part of the tampon means.

12. For use in the collection of blood in a body cavity, a tampon means and at least one device having a blood receiving interior carried by said tampon means for receiving and holding blood which is accessible in the device upon removal of the tampon means from the body cavity, said device including a blood preservative in said interior.

13. The combination of claim 12 and wherein the blood preservative is citric acid.

*14. In a method as recited in claim 1 and wherein said blood preservative is preliminarily situated in the interior of said device prior to introduction thereof into the body cavity.*

* * * * *